United States Patent [19]

Lavie et al.

[11] Patent Number: 5,047,435
[45] Date of Patent: Sep. 10, 1991

[54] ANTIVIRAL COMPOSITIONS CONTAINING AROMATIC POLYCYCLIC DIONES AND METHOD FOR TREATING RETROVIRUS INFECTIONS

[75] Inventors: David Lavie, Rehovot, Israel; Daniel Meruelo, Scarborough; Gad Lavie, New York, both of N.Y.; Michel Revel, Rehovot, Israel; Vincent Vande Velde, Boncelles, Belgium; Dalia Rotman, Rehovot, Israel

[73] Assignees: New York University, New York, N.Y.; Yeda Research and Development Company, Ltd., Rehovot, Israel

[21] Appl. No.: 328,767

[22] Filed: Mar. 27, 1989

Related U.S. Application Data

[63] Continuation-in-part of Ser. No. 84,008, Aug. 10, 1987, abandoned, which is a continuation-in-part of Ser. No. 82,700, Aug. 7, 1987, Pat. No. 4,898,891.

[30] Foreign Application Priority Data

Aug. 8, 1986 [IL] Israel ................................... 79661

[51] Int. Cl.$^5$ .................... A61K 31/015; A61K 45/08; A61L 2/18; A61L 15/00
[52] U.S. Cl. .................................. 514/732; 514/724; 514/738; 514/762; 514/764
[58] Field of Search ............... 514/732, 738, 724, 762, 514/764

[56] References Cited

U.S. PATENT DOCUMENTS

| | | | |
|---|---|---|---|
| 2,707,704 | 5/1955 | Brockmann et al. | 204/157.91 |
| 4,209,532 | 6/1980 | Wheeler | 514/520 |
| 4,338,122 | 7/1982 | Wheeler | 514/519 |
| 4,472,393 | 9/1984 | Shapiro | 514/176 |
| 4,540,700 | 9/1985 | York, Jr. | 514/278 |

OTHER PUBLICATIONS

Chemical Abstracts 66:88613y (1967).
Sedariston Product Information. Steiner Arzneinittel Ostpreubendamm, 72–74, 1000 Berlin.
Brockmann, H. H., Progress in Organic Chemistry, vol. I, Cook, J. W. ed., pp. 64–82, Academic Press, NY, 1952.
Banks, J. H., et al., Aust. J. Chem., 29: 1509–1521, 1976.
Roderwald, G., et al., Angew, Chem. Int. Ed. Eng., 16: 46–47, 56, 1977.
Adamski, R. et al., Chem. Abs., 75: 183, 1971, Abstract 91286k.
Weiss, U. et al., Progress in Organic Chemistry, 52: 1–71, 1987.
Muldner, H. et al., Arzneim.-Forsch., 34: 918, 1984.
Okpanyi, S. N. et al., Arzneim.-Forsch. 37: 10, 1987.
Brockmann, H. et al., Tetrahedron Letters 23: 1991–1994, 1974.
Daniel, K., Hippokrates 19: 526 (1949) (Chem. Abstr. 46:9721e, 1952).
Song, P-S. et al., Biophys. J. 35: 551–555, 1981.
Derbentseva, N. A., Chem. Abstr. 78: 67530, 1973.
Mishenkov, E. L. et al., Chem. Abstr. 85: 187161Y, 1976.
Brockmann, H. et al., Chem. Ber, 90:2480 (1957) (Chem. Abstr. 52:163, 1958).
Brockmann, H. et al., Chem. Ber. 90: 2302, 1957.
Japanese Patent Appln. 84–304493/49, Published 10/29/84 Abstract Only.
Merck Index 8th Ed., Staher, O. G., Edition, p. 558, 1968.
Daniel Meruelo et al., Proc. Natl. Acad. Sci., USA, vol. 85, pp. 5230–5234, 1988.
Brockmann et al., Tetrahedron Letters 1: 37–40, 1975.
Halm, Ivan, Gyogyszereszet 23: 217–218, 1973.

*Primary Examiner*—Nathan M. Nutter
*Attorney, Agent, or Firm*—Darby & Darby

[57] ABSTRACT

Pharmaceutical formulations comprising aromatic polycyclic dione compounds useful for treating mammals suffering from diseases caused by retroviruses are disclosed herein. A method for treating mammals suffering from retrovirus infections is also disclosed.

30 Claims, 2 Drawing Sheets

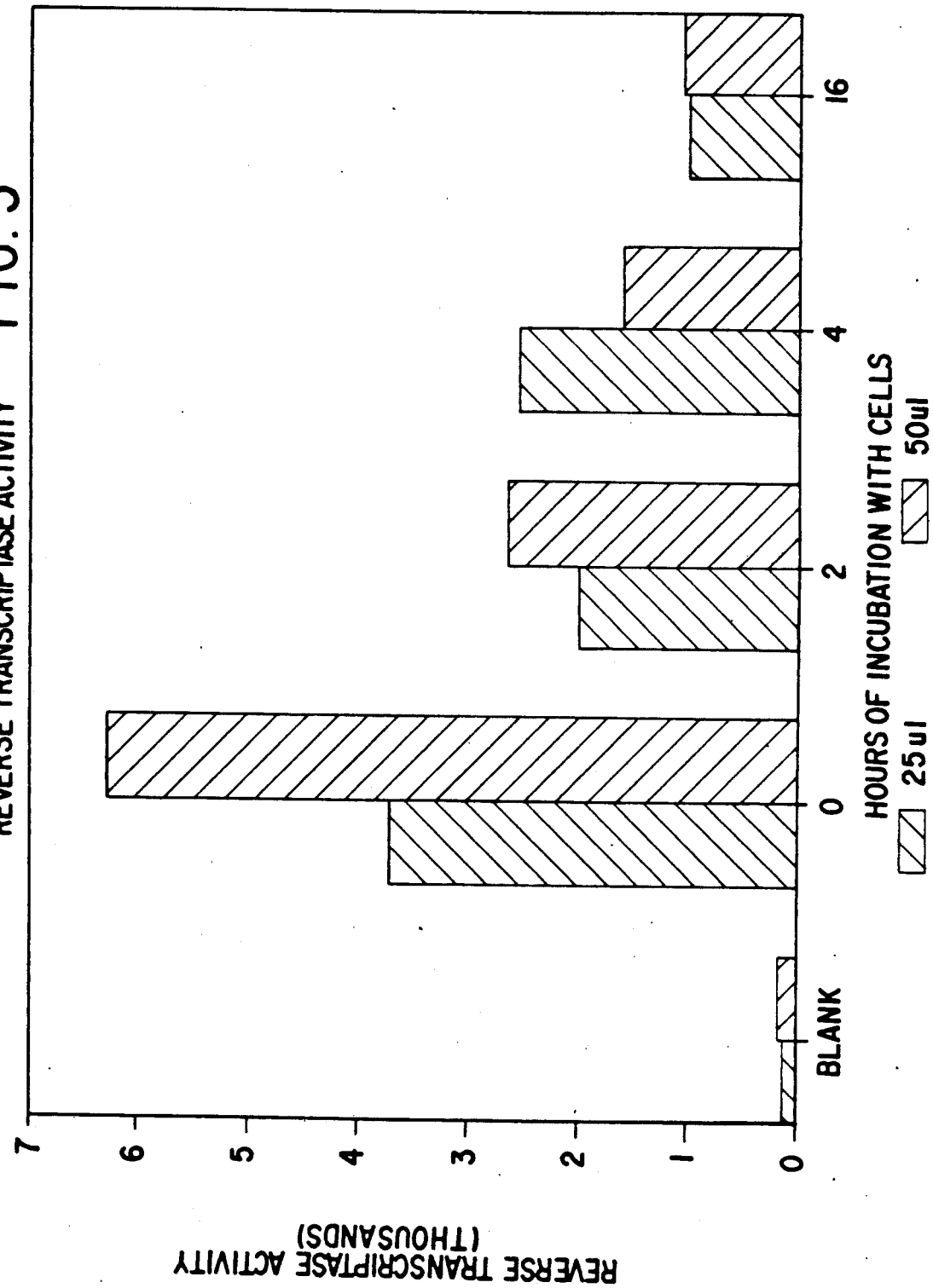

ANTIVIRAL COMPOSITIONS CONTAINING AROMATIC POLYCYCLIC DIONES AND METHOD FOR TREATING RETROVIRUS INFECTIONS

PRIOR RELATED APPLICATION

This application is a continuation-in-part of copending application Ser. No. 084,008, filed Aug. 10, 1987, and now abandoned which application is a continuation-in-part of the copending U.S. Pat. application Ser. No. 082,700 now U.S. Pat. No. 4,898,841 entitled Antiviral Compositions of David Lavie, Michel Revel, Dalia Rotman and Vincent Vandevelde filed Aug. 7, 1987. The entire disclosure of the parent application is incorporated herein by reference.

BACKGROUND OF THE INVENTION

This invention is related to pharmaceutical formulations comprising antiviral aromatic polycyclic dione compounds and methods of use thereof.

For many years the field of antiviral therapy has sought drugs that are capable of killing the invading pathogens without harming the host cell. The ability of viruses to physically invade a cell and to usurp the biochemical mechanisms of the cell in order to propagate their progeny, presents few unique biochemical features that can form the basis for selective inhibition of such viruses. Only a few compounds are known to possess selective antiviral activity. In particular, there are a wide variety of antiviral therapeutic agents, such as azidothymidine (AZT), dideoxycytidine, acyclovir, ribavirin, and vibaradine, which owe their selective toxicity to the fact that they can inhibit viral functions more efficiently than they can inhibit cellular functions. In general, these agents are targeted against viral polymerases, phosphorylases, and nucleotide kinases. The use of these drugs is limited due to their narrow spectrum of antiviral activity and their toxic side effects when administered systemically to a host organism over long periods of time.

Interferons are antiviral polypeptides which are currently in experimental therapeutic use in humans. However, their therapeutic value appears limited at the present time. The production and purification of human interferons require tedious procedures, the available quantities are limited and cytotoxic effects are also known to occur.

Recently it has become of great importance to find agents that are active against retroviruses, and in particular Human Immunodeficiency Virus (HIV) which is responsible for Acquired Immune Deficiency Syndrome.

Therefore, the art is constantly seeking new antiviral agents and in particular agents that are effective against retroviruses, which display high virus killing power with low cellular toxicity and have proven to be resistant to many conventional anti-viral agents.

OBJECTS OF THE INVENTION

It is an object of the present invention to provide therapeutic agents having antiviral activity and low cellular toxicity.

Another object of the present invention is to provide a method employing such therapeutic antiviral agents to treat a mammal suffering from retrovirus infections and diseases caused by such retroviruses.

A further object of the present invention is to provide pharmaceutical formulations for treating mammals suffering from retrovirus infections.

SUMMARY OF THE INVENTION

It has now been unexpectedly discovered that certain aromatic polycyclic dione compounds, exemplified by hypericin and pseudohypericin which are present in plants of the Family Hypericum (St. Johnswort) and which have been isolated from the plant *Hypericum triquetrifolium*, are effective against retroviruses including, for example, Friend Leukemia Virus (FV), Radiation Leukemia Virus (RadLV) and human immunodeficiency virus (HIV, also known as HTLV III).

The present invention provides pharmaceutical formulations for treating mammals suffering from diseases caused by retroviruses comprising an amount effective to inhibit such viruses of hypericin, pseudohypericin or mixtures thereof. The formulations may also include physiologically-acceptable carriers and salts.

In another aspect, the present invention provides a method for treating mammals suffering from diseases caused by retroviruses which comprises administering to mammals afflicted with a retrovirus infection an effective amount for treating such retrovirus infection of hypericin, pseudohypericin or mixtures thereof.

These and other aspects of the present invention will be apparent to those of ordinary skill in the art in light of the present description, accompanying claims and the appended drawings.

BRIEF DESCRIPTION OF THE DRAWINGS

FIG. 3 is a bar graph illustrating the inhibition of reverse transcriptase activity of Radiation Leukemia virus-infected mouse cells after treatment with pseudohypericin.

DETAILED DESCRIPTION OF THE INVENTION

Figure 1:
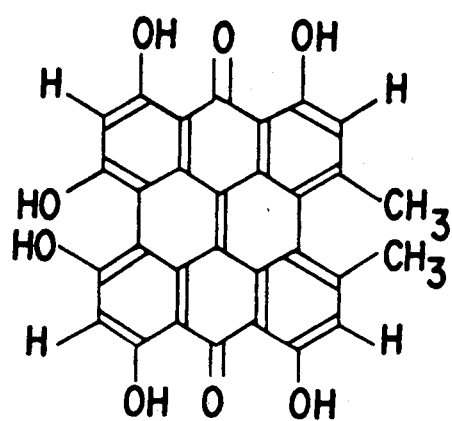
FIG. 1 is a diagram showing the chemical structure of hypericin.

It has now been unexpectedly discovered that certain aromatic polycyclic diones including hypericin and pseudohypericin are antiviral agents that are highly active against retroviruses. The anti-retroviral agents are compounds which have been isolated from the perennial plant *Hypericum triquetrifolium*.

As used herein, the term retrovirus refers to viruses containing an RNA genome and RNA-dependent DNA polymerase (reverse transcriptase) enzymic activity. All retroviruses have common morphological, biochemical and physical properties that justify their inclusion into a single virus family. These parameters are summarized in Table A below.

TABLE A
GENERAL PHYSICAL PROPERTIES OF KNOWN RETROVIRUSES

| | |
|---|---|
| Nucleic acid | linear positive-sense single-stranded RNA (60S–70S) composed of identical subunits (30S–35S); 5' structure ($m^7G^5ppp^5NmpNp$); polyadenylated 3' end; repeated sequences at 3' and 5' ends; tRNA base-paired to genome complex |
| Protein | about 60% by weight; gag, internal structural proteins; pol, reverse transcriptase; env, envelope proteins |
| Lipid | about 35% by weight; derived from cell |

TABLE A-continued
GENERAL PHYSICAL PROPERTIES OF KNOWN RETROVIRUSES

| | |
|---|---|
| | membrane |
| Carbohydrate | about 4% by weight; associated with envelope proteins |
| Physiochemical properties | density 1.16–1.18 g/ml in sucrose, 1.16–1.21 g/ml in cesium chloride; sensitive to lipid solvents, detergents, and heat inactivation (56° C., 30 min); highly resistant to UV- and X-irradiation |
| Morphology | spherical enveloped virions (80–120-nm diameter), variable surface projections (8-nm diameter), icosahedral capsid containing a ribonucleoprotein complex with a core shell (nucleoid) |

All retroviruses have similar overall chemical compositions. In general, they comprise about 60–70% protein, 30–40% lipid, 2–4% carbohydrate, and about 1% RNA. The envelope of retroviral particles is derived from the cell-surface membrane, and most, if not all, of the lipids in viral particles are located in the unit-membrane envelope of the virion Non limiting examples of retroviruses include Friend Leukemia Virus (FV), Radiation Leukemia Virus (RadLV) and Human Immunodeficiency Virus (HIV).

It has now been surprisingly discovered that the aromatic polycyclic dione compounds of the present invention inhibit the replication of Friend Leukemia virus and Radiation Leukemia virus, both in vivo and in vitro in mice. Even more surprisingly, this inhibition occurs without any significant toxicity to the recipient mammals, as shown in the examples below, wherein liver function assays, such as the levels of the enzymes lactate dehydrogenase (LDH) and serum glutamyl aminotransferase (SGOT) and those of bilirubin, which were increased due to FV infection (and are associated with the pathogenic effects of this virus) were returned to near normal values after administration of the antiviral compounds of the present invention.

The Merck Index (10th Ed. p. 710) discloses that hypericin is an antidepressant and that "small quantities appear to have a tonic and tranquilizing effect on the human organism." In addition, hypericin has been said to produce photosensitivity upon ingestion; Oxford, Raistick *Biochem J.* 34, 790 (1940).

Hypericin and pseudohypericin both display antiviral activity when administered to mice after retroviral infection. Hypericin was effective in inhibiting RadLV infection and pseudohypericin showed inhibitory activity against FV infection in mice as shown in Example II below. Moreover, a 50:50 mixture of hypericin and pseudohypericin led to an almost complete inhibition of the reverse transcriptase enzyme activity of RADLV-infected mouse cells in culture, as shown in Example 2 below. The same level of inhibition can be achieved by administering either hypericin or pseudohypericin alone.

The aromatic polycyclic diones appear to be capable of crossing the blood-brain barrier, as they have been previously administered as tranquilizing agents to humans. This is significant because, in the case of HIV, infection of the brain and central nervous system has been observed in infected individuals. It is also known that HIV can infect cells of the brain and central nervous system. Indeed, it has been recently found that gp120, a virally encoded polypeptide, is directly cytotoxic to cells of neuronal origin. Therefore, treatment of mammals suffering from diseases caused by these viral agents is a most important application of the present invention.

Hypericin and pseudohypericin, the aromatic polycyclic diones of the present invention can be used in treating mammals suffering from infections caused by retroviruses. These antiviral dione compounds are preferably obtained by extracting them from plants of the species Hypericum as detailed in Example 1 below, or alternatively may be chemically synthesized using the methods of Brockmann, M. et al, U.S. Pat. No. 2,707,704, issued May 3, 1955 and of Brockmann, H. et al *Tetrahedron Letters* 23:1991–1994, 1974, both incorporated herein by reference. Due to the wide distribution and availability of the St. Johnswort plant throughout the world and the relatively convenient and inexpensive procedure for the extraction and purification of the compounds of the present invention (as detailed in Example I below), the extraction procedure is preferred when small amounts (i.e. grams) are desired. However, for the production of large scale amounts (kilograms and greater) chemical synthesis is preferred.

Hypericum is a genus from the family Guttifereae. It has been related also to the families Hypericaceae and Clusiaceae. The genus is geographically fairly widely distributed. It is known for its content of ether-containing oils, and for the occurrence in small glands of red fluorescent pigments, represented among others by the aromatic polycyclic structural compounds hypericin and pseudohypericin (FIG. 1). Plants of the genus Hypericum have been reported to grow in very wide areas in Middle and Eastern Europe, Asia, North and South Africa. Additionally, there are reports of its occurrence in certain parts of the American continent, Australia and New Zealand. The plant is indexed in *The Audubon Society Field Guide to North American Wild Flowers, Eastern Region*, pg. 558, Chanticleer Press, Inc., N.Y., the disclosure of which is incorporated by reference.

The aromatic polycyclic diones of the present invention can be utilized for the treatment of mammals suffering from diseases caused by retroviruses such as Acquired Immune Deficiency Syndrome (AIDS). Due to their potency and lack of cellular toxicity, the aromatic polycyclic diones of the invention will be particularly useful as specific antiviral therapeutic agents for these disorders. Currently there are no broad spectrum agents available to treat these retroviral infections without concurrent cytotoxicity.

The present invention further includes salts or other derivatives of hypericin or pseudohypericin which retain their anti-viral activity. Salts in which the base is of the alkaline or amine type are particularly comprehended within the scope of the present invention.

When employed in vivo to treat AIDS, viremia (i.e. the presence of virus in the blood stream) or sepsis (viral contamination of bodily fluids) caused by retroviruses, the compounds of the present invention may be administered orally, topically or preferably parenterally, and most preferably intravenously at dosages which can be broadly defined as follows:

Antiretroviral compositions containing hypericin, pseudohypericin, salts or mixtures thereof as the active ingredients, can be used at dosages containing from about 0.001 micrograms to about 100,000 micrograms per kilogram bodyweight per treatment, preferably between about 1 microgram and about $5 \times 10^4$ micrograms per kilogram of bodyweight per treatment, and most preferably between about 100 micrograms and $5 \times 10^4$ micrograms per kilogram bodyweight per treatment.

The duration and number of doses or treatments required to control a particular retroviral disease will vary from subject to subject, depending upon the severity and stage of the illness and the subject's general condition and will also depend on the specific antiretroviral activity of each aromatic polycyclic dione compound, as well as the toxicity (if any) of the compound. The total dose required for each treatment may be administered in divided doses or in a single dose. The antiviral treatment may be administered daily, more than once daily, one or two times a week, or as determined by the subject's condition and the stage of the disease.

The present inventors have also discovered that the antiretroviral activity of hypericin is a function of the frequency of treatment. For example, in mouse studies, a single dose of ten micrograms per mouse was less effective than a single dose of 100 micrograms per mouse, as expected. However, administration of 10 micrograms every day for ten days was less effective than even a single 10-microgram dose. By contrast, administration of 10 micrograms once a week was as effective as the single 10-microgram dose. This indicates that the frequency of treatment effects its efficacy. While the foregoing observations in mice may not be applicable to other mammals or humans, those skilled in the art will appreciate that the frequency of treatment is subject to optimization, which can be determined by routine experimentation according to methods well known in the art, e.g. by establishing a matrix of dosage and frequency and assigning a group of experimental subjects to each point of the matrix. Design of this experiment should preferably also take into account the tissue accumulation properties of the compounds of the present invention.

The present invention also provides pharmaceutical compositions and formulations for treating retroviral infections. The compounds of the present invention can be incorporated in conventional, solid and liquid pharmaceutical formulations (e.g. tablets, capsules, caplets, injectable and orally administrable solutions) for use in treating mammals that are afflicted with retroviral infections. The pharmaceutical formulations of the invention comprise an effective antiretroviral amount of the compounds of the present invention (as disclosed above) as the active ingredients. For example, a parenteral therapeutic composition may comprise a sterile isotonic saline solution containing between about 0.001 micrograms and about 100,000 micrograms of the aromatic polycyclic dione compounds of the present invention as described above. It will be appreciated that the unit content of active ingredients contained in an individual dose of each dosage form need not in itself constitute an effective amount since the necessary effective amount can be reached by administration of a plurality of capsules, tablets, injections or combinations thereof.

Each formulation according to the present invention may additionally comprise inert constituents including pharmaceutically-acceptable carriers, diluents, fillers, salts, and other materials well-known in the art the selection of which depends upon the dosage form utilized and the particular purpose to be achieved according to the determination of the ordinarily skilled artisan in the field. For example, tablets may be formulated in accordance with conventional procedures employing solid carriers well known in the art. Examples of solid carriers include, starch, sugar, bentonite, silica and other commonly used carriers. Propylene glycol, benzyl alcohol, isopropanol, ethanol, dimethylsulfoxide (DMSO) dimethylacetamide or other biologically acceptable organic solvents or aqueous solutions (e.g. water with a pH higher than 7 and preferably about 8) may be used as diluents, carriers or solvents in the preparation of solid and liquid pharmaceutical formulations containing the anti-retroviral compositions of the present invention. Further nonlimiting examples of carriers and diluents include carbohydrates, albumin and/or other plasma protein components such as low density lipoproteins, high density lipoproteins and the lipids with which these serum proteins are associated. Such lipids include phosphatidyl choline, phosphatidyl serine, phosphatidyl ethanolamine and neutral lipids such as triglycerides. Additional lipid carriers include without limitatin tocopherol, retinoic acid and cyclodextranes. Semisolid formulatins such as those well-known in the art (e.g. supporitories) are also contemplated.

Preferred parenteral dosage forms may comprise for example an isotonic saline solution, containing between about 0.1 micrograms and about 100,000 micrograms of the aromatic polycyclic dione compounds of the present invention.

Capsules employed in the present invention may be made from any pharmaceutically acceptable material, such as gelatin or cellulose derivatives. Sustained release oral and transdermal delivery systems are also contemplated.

The antiviral aromatic polycyclic dione compounds of the present invention may additionally be incorporated into liposomes for use as specific drug carriers. Such liposomes may also comprise other active agents e.g., specific anti-HIV antibodies directed against viral proteins expressed by virally infected cells such as HIV p120, p41 and p24 (as well as glycosylated forms thereof) to act as specific targeting agents.

The aromatic polycyclic diones of the present invention may be ideally-suited for co-administration with other agents such as immune system cells, factors such as T-cells or interleukin-2, cytotoxic agents, lymphokines such as interferons or the like, that are known to have some effectiveness against retroviruses.

The present invention is described below in specific working examples which are intended to illustrate the invention without limiting the scope thereof.

EXAMPLE I

Extraction of Hypericin and Pseudohypericin from St. Johnswort

Hypericin, ($C_{30}H_{16}O_8$, molecular weight 504.43) referred to herein as Hy, and pseudohypericin ($C_{30}H_{16}O_9$ referred to herein as Ps, molecular weight 520.43) were obtained as detailed below.

The herb of the whole St. Johnswort plant was harvested at its flowering time, (July through October in the Eastern hemisphere), dried at 55° C., cut and milled, and then extracted with acetone (about 5-10 liters per kg). One kilogram of the material was placed in a soxhlet (Kimax, available from Fisher Scientific, New Brunswick, N.J.) and extracted until the extracting solvent was colorless (about five to ten hours). The solution containing the aromatic polycyclic diones had a red fluorescent color with absorption and fluorescence spectra as described in Scheibe *Schentag. Ber.* 75:

2019, 1942, Brockmann, M., Natureweiss 38: 47, 1951, both incorporated herein by reference.

The solvent (containing the aromatic polycyclic diones) was evaporated under reduced pressure to complete dryness of the residue, yielding 95 grams. This residue was then further fractionated on a chromatographic column, packed with silica gel 60 (0.06–0.20 mm, Malinckrodt, American Scientific Products, McGaw Park, Ill.). A dry chromatographic procedure was utilized whereby 25 grams of the above obtained residue was dissolved in about 500 ml acetone, added to an equal amount of silica gel 60, and evaporated on a rotavapor (Buchi, American Scientific Products) with swirling until the mixture was homogeneous and dry. The mixture was then placed on top of a column containing one kilogram of silica gel 60 and eluted with chloroform until the solvent reached the bottom of the column. This was followed by washing the column with a solvent mixture comprising chloroform-acetone-methanol, 75:15:10 (Vol/Vol/Vol). When the red color became 1/5 of the original intensity, the concentration of chloroform was reduced and the column eluted with a solvent mixture comprising chloroform-acetone-methanol in the ratio of 55:15:10 respectively (Vol/Vol/Vol). Fractions of 250 ml were collected. Each fraction was monitored on thin layer chromatoplates (VWR, San Francisco, Calif.) and the $R_f$ value of the two main red fluorescent spots under ultraviolet light at 254 nm was determined. The developing solvent mixture was chloroform-acetone-methanol, 55:15:10 as above. The chromatography was completed in about two days.

Further purification and separation of the two main components was obtained by two rounds of flash chromatography using a silica gel 60 (mesh 0.04–0.06) under pressure as described in *Gas Chromatography. Principles, Techniques and Applications.* A.B. Littlewood, ed. Academic Press. New York 1970; Still, W.C. et al., *J. Org. Chem.* 43: 2923–2925, 1978, incorporated herein by reference.

Two main components were identified: hypericin (Hy), $R_f$ 0.45, in a yield of 0.19 grams; and pseudohypericin (Ps), $R_f$ 0.35, in a yield of 0.73 grams. The NMR spectrum analysis of the two components were the same as those previously reported (Brockmann, H, et al, *Tetrahedron Letters* 1:37, 1975, incorporated by reference).

The compounds were stored at 4° C. in absolute ethanol, in the dark, until use.

EXAMPLE II

Antiviral Activity in Mammals

The effects of the compounds of the present invention on the infection of mammals with the retroviruses Friend Leukemia Virus (FV) and Radiation Leukemia Virus (RadLV) was examined as follows.

(1) Friend Leukemia Virus Infection

Friend Leukemia virus (FV) an aggressive retrovirus induces an acute erythroleukemia in sensitive strains of mice such as BALB/c and NIH SWISS mice (as described in Friend, C. *J. Exp. Med.* 105: 307–324, 1957; Friend, C. et al *Nat. Cancer Inst. Monogr.* 22: 505–522, 1966; Friend, C. et al *Proc. Natl. Acad. Sci. U.S.A.* 68: 378–383, 1971, all incorporated by reference herein). The malignant transformation is the result of the combined activities of the spleen focus forming virus (SFFV) and the ecotropic murine Friend Leukemia helper virus (F-MuLv). The acute erythroleukemia is characterized by hepatosplenomegaly (a marked increase in the size of the spleen and liver) and a severe anemia.

Friend Leukemia virus was prepared by homogenizing the enlarged spleen of a mouse previously infected with FV, 10 days after intravenous virus injection. The spleen was homogenized in phosphate buffered saline in a volume equal to 10 times the weight of the isolated spleen.

The effects of Hy and Ps on the increase in spleen size (splenomegaly) of BALB/c mice (Jackson Labs, Bar Harbor, Me.) was examined. In these experiments, the virus ($10^6$ focus forming units—FFU) was inoculated intravenously, and the indicated doses of the antiviral compounds of this invention were administered to the BALB/c mice intraperitoneally 24 hours later. The animals were then sacrificed ten days later and their spleens weighed. The results are summarized in Table 1 below.

TABLE 1

The effect of administering compound Ps (diluted in phosphate buffered saline with 1% ethanol) on the splenomegaly in BALB/c mice following inoculation with Friend erythroleukemia virus.

| Control Mice (PBS) | FV inoculated Mice ($10^6$ FFU) |
|---|---|
| 0.2094 Spleen weight (gms) | 1.0272 Spleen weight (gms) |
| 0.1834 Spleen weight (gms) | 0.9596 Spleen weight (gms) |
| 0.1790 Spleen weight (gms) | 1.2432 Spleen weight (gms) |
| 0.1669 Spleen weight (gms) | 1.1174 Spleen Weight (gms) |
| $\bar{x} = 0.1846 \pm 0.0178$ | $\bar{x} = 1.0865 \pm 0.1226$ |
|  | Net change from control = 0.9019 |
| Friend Virus ($10^6$ FFU) + PS 80 mcg/mouse | Friend Virus ($10^6$ FFU) + 2 injections PS 80 mcg/mouse |
| 0.2831 Spleen weight (gms) | 0.2457 Spleen weight (gms) |
| 0.2761 Spleen weight (gms) | 0.3400 Spleen weight (gms) |
| 0.2215 Spleen weight (gms) | 0.2938 Spleen weight (gms) |
| 0.1810 Spleen weight (gms) | 0.1956 Spleen weight (gms) |
| $\bar{x} = 0.2404 \pm 0.0482$ | $\bar{x} = 0.2687 \pm 0.0621$ |
| Net change from control = 0.0558 | Net change from control = 0.0841 |
| % Inhib = 93.82 | % Inhib = 90.70 |
| Control Mice (PBS) | Friend Mice ($2 \times 10^5$ FFU) |
| 0.2094 Spleen weight (gms) | 0.8911 Spleen weight (gms) |

TABLE 1-continued

The effect of administering compound Ps (diluted in phosphate buffered saline with 1% ethanol) on the splenomegaly in BALB/c mice following inoculation with Friend erythroleukemia virus.

| 0.1834 Spleen weight (gms) | 0.9211 Spleen weight (gms) |
|---|---|
| 0.1790 Spleen weight (gms) | 0.8004 Spleen weight (gms) |
| 0.1669 Spleen weight (gms) | 0.8662 Spleen weight (gms) |
| $\bar{x} = 0.1846 \pm 0.0178$ | $\bar{x} = 0.8697 \pm 0.0513$ |
|  | Net change from control = 0.6851 |
| Friend Virus (2 × 10⁵ FFU) + PS 80 mcg/mouse | Friend Virus (2 × 10⁵ FFU) 2 inject PS 80 mcg/mouse |
| 0.3457 Spleen weight (gms) | 0.4924 Spleen weight (gms) |
| 0.2784 Spleen weight (gms) | 0.2469 Spleen weight (gms) |
| 0.2208 Spleen weight (gms) | 0.2722 Spleen weight (gms) |
| 0.1791 Spleen weight (gms) | 0.2438 Spleen weight (gms) |
| $\bar{x} = 0.2560 \pm 0.0723$ | $\bar{x} = 0.3138 \pm 0.1197$ |
| Net change from control = 0.0714 | Net change from control = 0.1292 |
| % Inhib = 89.58 | % Inhib = 81.15 |

The data in Table 1 show the inhibition of splenomegaly, with median inhibition of 93.8%, following a single injection of 80 micrograms per mouse of Ps. A median inhibition of 89.6% in spleen enlargement was observed when 80 micrograms per mouse of Ps was administered in a single injection to mice that had previously been inoculated with 0.5 ml of the virus preparation (corresponding to 2×10⁵ FFU of virus). When two daily consecutive injections of Ps, each comprising 80 micrograms per mouse of the compound were administered, the median inhibition of splenomegaly was 90.7% with a viral preparation containing 10⁶ FFU and 81.7% with a viral preparation containing 2×10⁵ FFU (Table 1).

The above results show a marked decrease in the malignant transformational capacity of the Friend Leukemia Virus (as measured by decreased splenomegaly) following the intraperitoneally administration of Ps 24 hours after infection.

(2) Co-administration with Friend Leukemia Virus

A different experimental design was also tested involving the simultaneous intravenous co-administration of Ps with the FV complex. In this case, the viral preparation was mixed with Ps at various concentrations and the mixture was injected into the mouse tail vein in a final volume of 0.5 ml. The mice were sacrificed ten days later, the spleens weighed and the level of inhibition of splenomegaly subsequently determined. The results are summarized in Table 2.

TABLE 2

The effect of intravenous co-administration of pseudohypericin (diluted in PBS with 1% EtOH) with FV, on viral-induced splenomegaly.

Spleen Weights (grams)

| Controls | | | Expt 1 | Expt 2 | Expt 3 |
|---|---|---|---|---|---|
| PBS | PBS + 1% EtOH | FV | FV + PS 5 mcg | FV + PS 20 mcg | FV + PS 50 mcg |
| 0.1304 | 0.1862 | 1.1499 | 0.3425 | 0.1655 | 0.1830 |
| 0.1490 | 0.1567 | 1.0657 | 0.3766 | 0.1426 | 0.1674 |
| 0.1362 | 0.1386 | 0.9597 | 0.4005 | 0.1433 | 0.1422 |
| 0.1515 | $\bar{x} = 0.1605 \pm$ | 1.1347 | 0.4255 | 0.1966 | 0.1365 |
| $x = 0.1417 \pm$ 0.0101 | 0.0240 | $\bar{x} = 1.0774 \pm$ 0.0866 | $\bar{x} = 0.3862 \pm$ 0.0353 | $\bar{x} = 0.1614 \pm$ 0.0253 | $\bar{x} = 0.1572 \pm$ 0.0217 |
| % inhibition as compared to the group receiving Ps in PBS + 1% EtOH = | | | 75.44% | 100% | 100% |

As shown in Table 2 above, 100% inhibition of splenomegaly was found when Ps was administered with the viral complex at concentrations of 20 micrograms per mouse and 50 micrograms per mouse (average mouse weight approximately 150 grams). A mean inhibition of 75.44% was found when 5 micrograms per mouse was co-administered with the virus.

These results show the effectiveness of the compounds of the present invention in that as little as 5 micrograms per mouse was effective in inhibiting viral transformation by this aggressive RNA tumor virus.

(3) Effect of Ps on liver function of FV infected animals

As a further demonstration of the antiviral activity of Ps, the effect of FV infection, in the presence and absence of Ps, on liver functions was monitored by analyzing the serum of infected mice for liver-associated proteins.

BALB/c mice were inoculated with FV at a concentration of 2×10⁵ FFU. Each group of animals contained 4 mice, and analyses were done in pooled aliquots.

TABLE 3

EFFECT OF FRIEND VIRUS WITH OR WITHOUT PS (IN PBS WITH 1% EtOH) ON LIVER FUNCTIONS

| | CHOLEST mg/dl | Total PROTEIN gms/dl | ALBUMIN gms/dl | BU mg/dl | AP IU/liter | LDH IU/liter | SGOT IU/liter | SGPT IU/liter | GGT miu/ml |
|---|---|---|---|---|---|---|---|---|---|
| PBS | 122 | 5.7 | 3.3 | 0.2 | 226 | 1075 | 132 | 105 | 3 |
| IVFV | 118 | 5.5 | 3.4 | 0.4 | 200 | 6710 | 450 | 110 | 4 |

TABLE 3-continued
EFFECT OF FRIEND VIRUS WITH OR WITHOUT PS (IN PBS WITH 1% EtOH) ON LIVER FUNCTIONS

| | CHOLEST mg/dl | Total PROTEIN gms/dl | ALBUMIN gms/dl | BU mg/dl | AP IU/liter | LDH IU/liter | SGOT IU/liter | SGPT IU/liter | GGT miu/ml |
|---|---|---|---|---|---|---|---|---|---|
| IVFVIPPS | 109 | 5.7 | 3.4 | 0.1 | 226 | 3303 | 213 | 99 | ND |
| IPFV | 111 | 5.4 | 3.3 | 0.2 | 223 | 3330 | 245 | 100 | 3 |
| IPFVIVPS | 137 | 5.5 | 3.2 | 0.3 | 200 | 2305 | 244 | 135 | 4 |

PBS - Phosphate Buffered Saline
IVFV - Intravenous administration of Friend Virus
IVFVIPPS - Intravenous administration of Friend Virus, intraperitoneal injection of Ps compound
IPFV - Intraperitoneal administration of Friend Virus
IPFVIVPS - Intraperitoneal administration of Friend Virus, intravenous injection of Ps compound In Table 3, BU=Total Bilirubin, AP=Alkaline phosphatase, LDH=Lactate dehydrogenase, SGOT=-Serum glutamyl aminotransferase, SGPT=Serum glutamyl peptidyltransferase, and GGT=Gamma-glutamyl-transpeptidase.

As shown in Table 3, intravenous inoculation with FV led to an increase in LDH, SGOT and SGPT enzyme activity and to an increased total serum bilirubin accumulation in infected mice. Such increases are indicators of liver function damage, well-known in the art. Administration of Ps, both intravenously and intraperitoneally, led to a reduction in these virally-induced increases.

(4) Antiviral Effect on Radiation Leukemia Virus

Murine radiation leukemia virus (RadLV) was inoculated intrathymically into B10.T(6R) mice as described in Meruelo et al (supra). Groups of six mice were treated 24 hours later with 30 micrograms per mouse of compound Hy administered intraperitoneally in isotonic saline solution. The mice were sacrificed ten days later and the expression of Class I H-2 antigens determined by analysis with a fluorescence activated cell sorter (Ortho Cytofluorograph Model 50H, Ortho Diagnostic Systems, Westwood, Mass.) (FACS), using X-56 anti-H-2D$^d$ mouse monospecific antibodies (as described in Meruelo, et al supra; similar antibodies are available as ATCC No. HB75, American Type Culture Collection, Rockville, MD). The results are shown in Table 4 below.

TABLE 4
The effect of Hy and Ps on the increase in H-2 antigen expression in thymocytes after intrathymic inoculation of mouse radiation leukemia virus in B10.T(6R) mice.

| Base Line (untreated mice) | | Virus Induced (inoculated mice) | | 30 mcg/mouse Hy (inoculated with RadLV and Hy) | | 30 mcg/mouse PS | |
|---|---|---|---|---|---|---|---|
| % of cells stained with antibody | mean fluorescent intensity in fluorescent units | % of cells stained with antibody | mean fluorescent intensity in fluorescent units | % of cells stained with antibody | mean fluorescent intensity in fluorescent units | % of cells stained with antibody | mean fluorescent intensity in fluorescent |
| 94.1 | (606.8) | 97.3 | (752.9) | 76.7 | (625.5) | 97.4 | (713.3) |
| 76.0 | (515.7) | 91.7 | (599.0) | 77.2 | (596.9) | 94.3 | (639) |
| 45.1 | (440.3) | 92.5 | (599.6) | 96.3 | (723.6) | | |
| 76.0 | (518.7) | 94.0 | (703.1) | 84.8 | (663.5) | | |
| 89.5 | (596.7) | 96.3 | (729.2) | 54.0 | (513.6) | | |
| 87.4 | (558.8) | 97.3 | (719.9) | 97.8 | (657.3) | | |
| x̄ = 78.02 | | x̄ = 94.85 | | x̄ = 81.13 | | | |

(1) % inhibition = $100 - \left[ \frac{\text{(Treated 30 mcg)} - \text{(Base Line)}}{\text{Virus Induced} - \text{Base Line}} \right] \times 100 = 82\%$

Infection (RadLV)

The intrathymic inoculation of murine radiation leukemia virus in susceptible strains of mice results in the malignant transformation of the thymocytes and the development of overt leukemia (as described in Meruelo, D. et al J. Exp. Med. 147: 470–487, 1978, incorporated herein by reference). This transformation has been shown to be associated with the major histocompatibility complex (MHC) which determines resistance or susceptibility to the leukemogenic effects of the virus. Among the early events which follow the viral infection in some mouse strains is a dramatic increase in the cell surface expression of class I H-2 antigens. This increase is then followed by a reduction in the expression of these antigens after the malignant transformation and subsequent development of leukemia. The changes in H-2 antigen expression have been utilized to monitor viral infectivity and to determine the effects of Hy and Ps on the level of infectivity of this virus.

As can be seen from the data in Table 4, Hy exerted a significant inhibition in the increase in H-2 expression in four of the six mice tested (Table 4), indicating a significant reduction in the infective capacity of the virus following the intraperitoneal administration of compound Hy. This occurred as late as 24 hours after the initial viral inoculation. No effects on H-2 expression induced by RadLV were found with 40 compound Ps.

EXAMPLE III

Effects of Ps and Hy on RNA-Dependent DNA Polymerase (Reverse Transcriptase)

Retroviruses (RNA tumor viruses) carry within the virion the reverse transcriptase enzyme which, upon infection of the cell with the virus, recruits the cellular synthetic machinery and transcribes a complementary DNA (cDNA) copy of the virion RNA using the viral RNA genome as a template. The determination of levels of reverse transcriptase (RT) activity in the growth medium of cells infected with retroviruses is a well-known method with which to evaluate the release of infectious virus particles by cells and has been used to measure the antiviral activity of the components of the present invention. The effect of a mixture of both Hy and Ps at a concentration of 10 micrograms per ml (of each compound) on the RadLV RT activity was examined.

The mixture of the two compounds was administered 2, 4 and 16 hours post-infection and the supernatants were harvested and assayed for RT activity according to the method of Stephenson et al, *Virology* 48:749-756, 1972, and Weissbach et al, *J. Virol.* 10:321-327, 1972, both references incorporated herein by reference.

The assay was performed as follows:

a) Preparation of Virus

RadLV-infected lymphoblastoid cells, line B10.T(6R) were pelleted by centrifugation at 4° C., 3500 rpm for 15 minutes. The top ⅔ of the supernatant (10 ml) was removed for assay. The supernatant was then centrifuged at 40,000 rpm for 1 hour at 4° C. in 12 ml ultracentrifuge tubes, using a fixed-angle ultracentrifuge rotor (Ti70 rotor, Beckman Instruments, Fullerton, Calif.). The supernatant was carefully decanted and the tubes dried. The pellet was resuspended in 200 microliters of a buffer containing 0.02M Tris/HCl, pH 7.8, 0.1M NaCl, 0.001M dithiothreitol, and 0.2% Triton X-100. The mixture of the buffer and the virus-containing pellet was vortexed and incubated on ice for 30 minutes before use.

The reverse transcriptase assay was performed in a volume of 100 microliters containing the following components:

TABLE 5

| Reagent Stock | | ul of Stock per assay | final concentration per assay (100 ul) |
|---|---|---|---|
| sol'n A: | 0.5M Tris/HCl pH 7.8(37°) | | 50 mM |
| | 0.6M KCl | 10 ul | 60 mM |
| sol'n B: | 2.0 mM Mn Acetate | 10 ul | 0.2 mM |
| sol'n C: | 40 mM Dithiothreitol (DTT) | 5 ul | 2 mM |
| Triton X-100 (10%) | | 1 ul | 0.1% |
| poly(rA).(dT)$_{12}$ (10 A$_{260}$ U/ml)[1] | | 4 ul | 0.4 A$_{260}$/ml (20 mcg/ml) |
| dTTP (2 × 10$^{-4}$ M) | | 10 ul | 2 × 10$^{-5}$ M |
| $^3$H-dTTP (500 uCi/ml)[2] | | 10 ul | 5 uCi |
| | 2500 uCi/ml | 50 ul | |

[1] obtained from Pharmacia Fine Chemicals, Piscataway, NJ
[2] obtained from New England Nuclear, Boston, MA 50 microliters of the reaction mixture was mixed with 50 microliters of the above obtained supernatant and incubated for 1 hour at 30° C. The reaction was stopped by the addition of 0.1 ml of 0.06M sodium pyrophosphate, vortexed and incubated on ice. 2 ml of 10% trichloroacetic (TCA) containing 0.3M sodium pyrophosphate was added, the mixture vortexed and incubated on ice for 10-20 minutes. TCA-percipitable radioactivity was determined after filtrations of samples using glass fiber filters (2.4 cm Whatman GFC, Whatman, Clifton, N.J.). The results are shown in FIG. 2.

Figure 2:
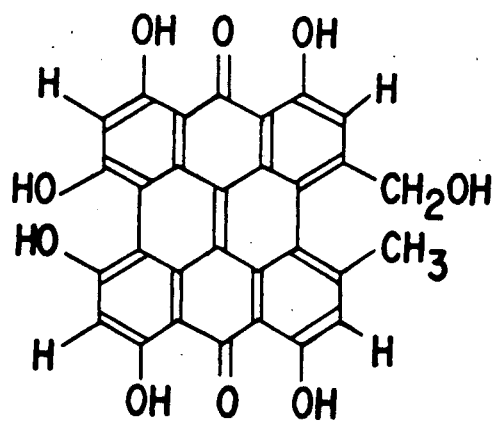
FIG. 2 is a diagram showing the chemical structure of pseudohypericin.

The data in FIG. 2 shows that incubation of virally-infected cells with the 50:50 mixture of Hy and Ps led to at least a 50% decrease in the detectable RT activity at 2 and 4 hours post infection and further inhibited this enzyme approximately 75% when assayed 16 hours post-infection.

EXAMPLE IV

Inhibition of HIV by the Compounds of the Present Invention

The activity of Ps, Hy and mixtures thereof against human immunodeficiency virus (HIV) may be investigated in the following manner. HIV-infected, OKT4+ lymphoblastoid cells, such as clone H9 (described in Popovic, M., et al, *Science* 224:497-500, 1984, incorporated by reference) is maintained in RPMI-1640 medium (GIBCO, Grand Island, N.Y.) containing 20% fetal calf serum (Flow Laboratories, Inglewood, Calif.). Triplicate cultures of cells, seeded at a concentration of about 4×10$^5$ cells per ml, are exposed to polybrene (2 micrograms per ml, Sigma Chemical Co., St. Louis, Mo.), infected with 2×10$^8$ HTLV III particles per 4×10$^5$ H9 cells, and cultured in the presence or absence of Ps, Hy and mixtures thereof as in Example 2 above.

The antiviral activity of the compounds of the present invention is determined by monitoring the reverse transcriptase activity and the expression of HIV proteins p24 and p17, as described in Sarin, P.S. et al, *J. Nat. Cancer Inst.* 78:663-665, 1987, incorporated herein by reference.

EXAMPLE V

Expression of HTLV III gag proteins p24 and p17.

H9 cells (2×10$^5$), either uninfected or HTLV III infected, are continuously exposed to various concentrations of Ps, Hy and mixtures thereof at concentrations between 5 and 100 micrograms per ml for 4 days. The percentage of cells expressing p24 and p17 gag proteins of HTLV III is determined by indirect immunofluorescence microscopy with the use of mouse monoclonal antibodies to HTLV-III p17 and p24 (available in numerous commercial sources such as those in HIV serum antigen detection kits from Abbott Labs, North Chicago, Ill., and from Du Pont, Wilmington, Del.). The positive cells are visualized by treatment with fluorescein-labeled goat anti-mouse IgG (Cappell Laboratories, Cochranville, Pa.). The experiments are performed in duplicate (at least three times).

EXAMPLE VI

Determination of reverse transcriptase activity

Uninfected H9 or H9 cells infected with HTLV-III (500 virus particles/cell) are exposed to various concentrations of Ps, Hy and mixtures thereof as above. At day 4, supernatants of the cultures are collected and virus particles are precipitated with polyethylene glycol and obtained by centrifugation as described above in Example 2 for FV. The virus pellet is suspended in 300 microliters of buffer containing 50 mM Tris-HCl (pH 7.5), 5 mM dithiothreitol, 250 mM KCl, and 0.25% Triton X-100. Reverse transcriptase activity in these samples is analyzed in a 50-ul reaction mixture containing 50 mM Tris-HCl (pH 7.5), 5 mM dithiothreitol, 100 mM KCl, 0.01% Triton X-100, 10 ul $dT_{15}rA_n$ as template primer, 10 mM $MgCl_2$, 15 uM [$^3$H]dTTP (New England Nuclear, Boston, Mass.), and 10 microliters of disrupted virus suspension. After incubation for 1 hour at 37° C. and subsequent addition of 50 micrograms of yeast tRNA (Sigma Chemical, St. Louis, Mo.), the incorporation into cold trichloroacetic acid-insoluble fraction is assayed as in Example 2 above. Assays are performed in duplicate and repeated three times.

What is claimed is:

1. A method for treating a mammal afflicted with a disease caused by a retrovirus which comprises administering to said mammal an effective anti-retroviral amount of a compound selected from the group consisting of hypericin, pseudohypericin, a pharmaceutically-acceptable salt of hypericin or pseudohypericin, and mixtures thereof.

2. The method of claim 1 which comprises administering said effective amount orally.

3. The method of claim 1 which comprises parenterally administering said effective amount of said compound.

4. The method of claim 1 wherein said compound comprises hypericin.

5. The method of claim 1 wherein said compound comprises pseudohypericin.

6. The method of claim 1 wherein said compound comprises a mixture of hypericin and pseudohypericin.

7. The method of claim 1 which comprises administering said compound intravenously.

8. The method of claim 1 wherein said effective amount is between about 0.001 micrograms and about 100,000 micrograms per kilogram of body weight of said mammal.

9. A pharmaceutical formulation for treating mammals suffering from an infection caused by a retrovirus comprising an effective anti-retroviral amount of a compound selected from the group consisting of hypericin, pseudohypericin, a pharmaceutically-acceptable salt of hypericin or pseudohypericin, mixtures thereof and a pharmaceutically-acceptable carrier for diluent.

10. The pharmaceutical formulation of claim 9, wherein said compound comprises hypericin.

11. The pharmaceutical formulation of claim 9, wherein said compound comprises pseudohypericin.

12. The pharmaceutical formulation of claim 9 which comprises a mixture of hypericin and pseudohypericin.

13. The pharmaceutical formulation of claim 9 comprising a parenteral dosage form.

14. The pharmaceutical formulation of claim 9 comprising a solid oral dosage form selected from the group consisting of a tablet and a capsule.

15. The pharmaceutical formulation of claim 9 wherein said effective amount comprises between about 0.001 milligrams and about 100,000 milligrams of said compound.

16. The pharmaceutical formulation of claim 13 which comprises an injectable solution.

17. A method for inhibiting the proliferation of a retrovirus which comprises treating said retrovirus with an effective anti-retroviral amount of a compound selected from the group consisting of hypericin, pseudohypericin, a pharmaceutically-acceptable salt of hypericin or pseudohypericin, and mixtures thereof.

18. The method of claim 17 wherein said compound comprises hypericin.

19. The method of claim 17 wherein said compound comprises pseudohypericin.

20. The method of claim 17 wherein said compound comprises a mixture of pseudohypericin and hypericin.

21. The method of claim 17 wherein said retrovirus comprises Friend Leukemia virus.

22. The method of claim 17 wherein said retrovirus comprises Radiation Leukemia virus.

23. The method of claim 17 wherein said retrovirus comprises human immunodeficiency virus.

24. The method of claim 1 wherein said retrovirus comprises human immunodeficiency virus.

25. The method of claim 4 wherein said virus is human immunodeficiency virus.

26. The method of claim 5 wherein said virus is human immunodeficiency virus.

27. The pharmaceutical formulation of claim 9, wherein said compound comprises purified hypericin.

28. The pharmaceutical formulation of claim 9, wherein said compound comprises purified pseudohypericin.

29. A method for treating a mammal afflicted with Human Immunodeficiency Virus which comprises administering to said mammal an effective amount for treating Human Immunodeficiency Virus of at least one member selected from the group consisting of hypericin, pseudohypericin, a pharmaceutically-acceptable salt of hypericin or pseudohypericin, and mixtures thereof.

30. A pharmaceutical dosage form for treating a mammal afflicted with a retrovirus comprising an effective antiretroviral amount of hypericin in an oral dosage form.

* * * * *